United States Patent

Rostek, Jr.

Patent Number: 5,260,454
Date of Patent: Nov. 9, 1993

[54] BIS-PYRIMIDYL THIOL SULFENIMIDE COMPOUNDS

[75] Inventor: Charles J. Rostek, Jr., Bentleyville, Ohio

[73] Assignee: Monsanto Company, St. Louis, Mo.

[21] Appl. No.: 15,959

[22] Filed: Feb. 8, 1993

Related U.S. Application Data

[62] Division of Ser. No. 763,782, Sep. 23, 1991, Pat. No. 5,189,174, which is a division of Ser. No. 402,741, Sep. 5, 1989, Pat. No. 5,079,305.

[51] Int. Cl.$^5$ ............................................. C07D 403/12
[52] U.S. Cl. ................................... 544/296; 544/298; 544/299
[58] Field of Search ......................... 544/296, 298, 299

[56] References Cited

U.S. PATENT DOCUMENTS 2,321,305  6/1943  Messer ................................. 548/157
2,321,306  6/1943  Messer ................................. 548/332.7

(List continued on next page.)

FOREIGN PATENT DOCUMENTS 0417057  3/1991  European Pat. Off. .
2121522  11/1972  Fed. Rep. of Germany .
2233502  1/1973  Fed. Rep. of Germany .
1131810  2/1957  France .
1368623  6/1964  France .
280473  1/1972  U.S.S.R. .
478010  7/1975  U.S.S.R. .
504810  8/1976  U.S.S.R. .
1342046  12/1973  United Kingdom .
1345318  1/1974  United Kingdom .
1355801  6/1974  United Kingdom .

OTHER PUBLICATIONS

Article "Preparing N-Alkyl-and N-Cycloalkyblis-2-benzothiazolesulfen) amides" United States Rubber Co., Naugatuck Chemical Division, Naugatuck, Conn., 1959.

Journal de Pharmacie de Belgique vol. 39 No. 4, 1984; R. Lejeune et al.

Archiv der Pharmazie vol. 305 No. 6 May 1972; R. Neidlein et al.

*Primary Examiner*—Mukund J. Shah
*Assistant Examiner*—Y. N. Gupta
*Attorney, Agent, or Firm*—Gordon B. Seward

[57] ABSTRACT

Heterocyclic thiol sulfenimide compounds are useful as an accelerator in the curing of natural and/or synthetic rubbers. The compound can be represented by the formula $$A^1-S-\underset{\underset{R}{|}}{N}-S-A^2$$

wherein each of $A^1$ and $A^2$, independently, is at least one heterocyclic ring containing one or more nitrogen atoms therein, or at least one heterocyclic ring containing one or more nitrogen atoms therein and (1) one or more hydrocarbyl substituents, or (2) one or more electron withdrawing groups, or (3) one or more electron releasing groups, wherein $A^1$ alternatively is thiazyl or a dithiocarbamoyl, and wherein R is a (a) hydrogen atom, or (b) a hydrocarbyl radical having from 1 to 16 carbon atoms, or (c) the hydrocarbon radical of (b) wherein one or more of the carbon atoms is an oxygen atom, a nitrogen atom, or a substituted nitrogen atom wherein said substituted group is an alkyl and in combination with said nitrogen atom forms a heterocyclic ring having a total of from 1 to 7 carbon atoms, or (d) the hydrocarbyl radical of (b) containing a halogen, an amino, a cyano, an alkoxy, a hydroxy, or an alkoxycarbonyl. When the heterocyclic thiol sulfenimide compound is utilized as an accelerator for rubber, improved cure rates, longer scorch delay, and better reversion resistance are obtained in comparison to conventional sulfenamides.

2 Claims, 1 Drawing Sheet

VULCANIZATION PARAMETERS

U.S. PATENT DOCUMENTS

| | | | |
|---|---|---|---|
| 2,370,253 | 2/1945 | Messer | 548/167 |
| 2,860,142 | 11/1958 | Conly | 548/157 |
| 2,873,277 | 2/1959 | Sundholm | 548/157 |
| 2,889,331 | 6/1959 | Sundholm | 548/157 |
| 2,930,824 | 3/1960 | Sundholm | 525/349 |
| 3,071,592 | 1/1963 | Ladd | 548/521 |
| 3,151,122 | 9/1964 | Sundholm | 548/157 |
| 3,362,937 | 1/1968 | Kent | 427/393.5 |
| 3,394,126 | 7/1968 | D'Amico | 540/480 |
| 3,525,737 | 8/1970 | Kern | 540/525 |
| 3,549,650 | 12/1970 | D'Amico | 548/167 |
| 3,573,262 | 3/1971 | Morche | 525/348 |
| 3,671,503 | 6/1972 | Schubert | 525/348 |
| 3,737,431 | 6/1973 | Campbell | 544/135 |
| 3,770,826 | 11/1973 | Schubert et al. | 564/101 |
| 3,847,880 | 11/1974 | Trivette, Jr. et al. | 525/384 |
| 3,875,177 | 4/1975 | Maison | 548/261 |
| 3,997,605 | 12/1976 | Hopper | 560/312 |
| 4,166,864 | 9/1979 | D'Silva | 424/285 |

VULCANIZATION PARAMETERS

BIS-PYRIMIDYL THIOL SULFENIMIDE COMPOUNDS

This is a division of application Ser. No. 07/763,782, filed Sep. 23, 1991, now U.S. Pat. No. 5,189,174, which in turn is a division of application Ser. No. 07/402,741, filed Sep. 5, 1989, now U.S. Pat. No. 5,079,305.

FIELD OF THE INVENTION

The present invention relates to novel heterocyclic thiol-based sulfenimide compounds and to the preparation thereof.

BACKGROUND

Heretofore, numerous primary accelerators such as the various well known sulfenamides of 2-mercaptobenzothiazole, and to a lesser extent, sulfenimides of 2-mercaptobenzothiazole [also referred to as bis(sulfenamides)] have been utilized to cure natural and/or synthetic rubbers. While they improved upon the art preceding them, still faster cure rate, longer scorch delay, and better reversion resistance are desirable.

U.S. Pat. No. 2,321,305 to Messer relates to rubber vulcanization accelerators represented by the formula where AR is an arylene group; when n is 1, X is NH-alkyl, NH-aryl, N-diaryl, O-alkyl or O-aryl; when n is 2, X is oxygen, NH, N-alkyl, or N-alicyclic; when n is 3, X is N.

U.S. Pat. No. 2,321,306 to Messer also relates to rubber vulcanization accelerators of the type set forth in U.S. Pat. No. 2,321,305.

U.S. Pat. Nos. 2,860,142 to Conly; 2,873,277 to Sundholm; 2,889,331 to Sundholm; 3,151,122 to Sundholm; and 3,875,177 to Maison, all relate to bis(sulfenamides) (sulfenimides) of 2-mercaptobenzothiazole as accelerators. While referred to in the prior art as bis(sulfenamides), it is chemically correct to refer to these compounds as sulfenimides.

SUMMARY OF THE INVENTION

Novel heterocyclic thiol-based sulfenimides are provided. The compounds are generally made via the corresponding sulfenyl chloride, by reacting a diheterocyclic disulfide compound with a chlorine source in a suitable solvent. The intermediate sulfenyl chloride compound is then reacted with a primary amine in the presence of an acid acceptor usually at a low temperature to produce the heterocyclic thiol-based sulfenimide compound of the present invention. The compounds of the present invention when utilized as accelerators for curing natural rubber, synthetic rubbers such as polybutadiene or styrene-butadiene rubber, blends of synthetic rubbers such as natural rubber and polybutadiene, styrene-butadiene rubber and polybutadiene, or combinations thereof, result in improved cure rates as indicated by t90-t2 values, t25-t2 values and maximum rate of vulcanization (Vmax), better scorch delay, and reduced reversion in comparison with traditional or conventional sulfenamide accelerators such as 2-mercaptobenzothiazolyl-t-butyl sulfenamide (Santocure NS ®) and sulfenimides of 2-mercaptobenzothiazole. Increased cure rates are very desirable since faster rates of production of rubber articles can be obtained. Molded rubber articles can thus be removed from the mold at earlier times without the danger of undercure. While it is generally possible to increase the cure rate of a rubber compound (up to a point) by using combinations of accelerators and/or higher levels of accelerators, these changes are often accompanied by unacceptable losses of scorch delay or unacceptable increases in the moduli of the vulcanized articles. Longer scorch delay is desirable to provide a longer time for the rubber article to be shaped and molded before the onset of vulcanization. Reduced reversion is desirable because it results in a more stable network which imparts more favorable physical properties to the vulcanizate.

DETAILED DESCRIPTION OF THE INVENTION

Figure 1:
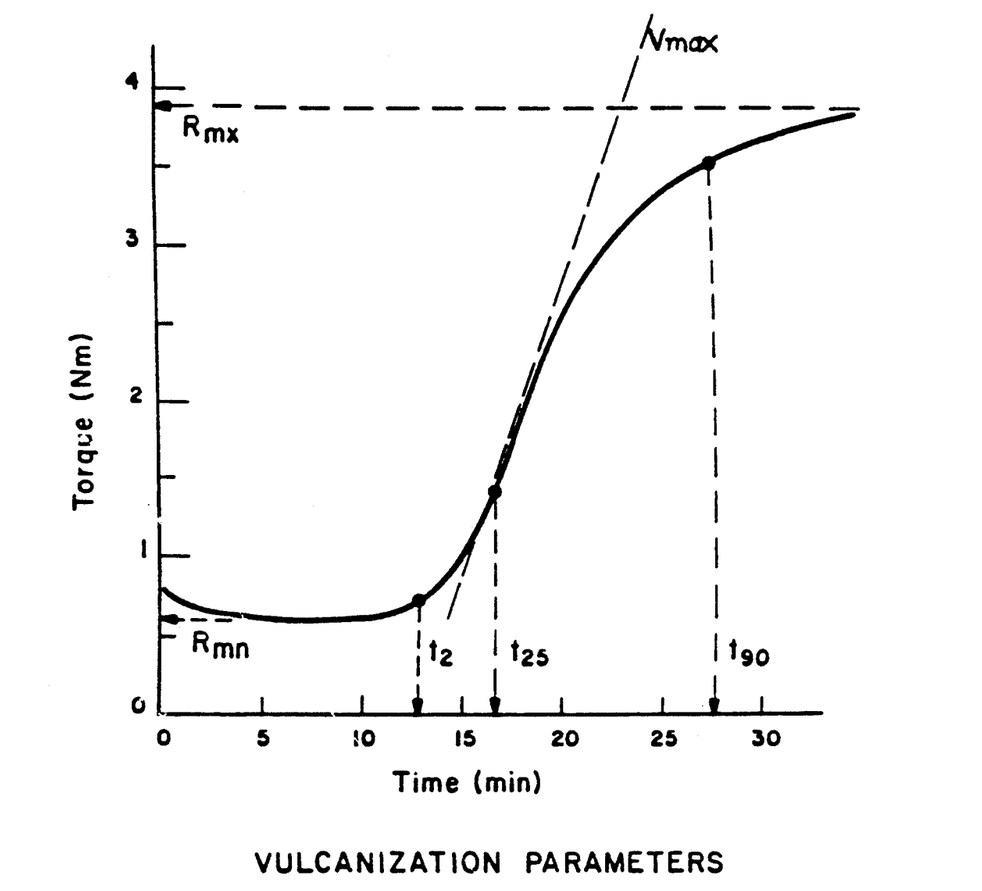
The drawing is a typical rheograph showing the parameters of the vulcanization.

The heterocyclic thiol-based sulfenimide compounds of the present invention generally can be represented by the following formula where each of $A^1$ and $A^2$, independently, is at least one heterocyclic ring containing one or more nitrogen atoms therein, or at least one heterocyclic ring containing one or more nitrogen atoms therein and (1) one or more hydrocarbyl substituents, or (2) one or more electron withdrawing radicals, or (3) one or more electron releasing radicals. Although the heterocyclic ring can contain three nitrogen atoms therein, it desirably contains no more than two nitrogen atoms therein with one nitrogen atom therein being preferred. When the heterocyclic ring contains one nitrogen atom therein, the sulfur atom can be located at the three or four position with the two position being highly preferred. However, at least one of said $A^1$ or said $A^2$ group is not a benzothiazolyl group, that is, is free therefrom, and furthermore at least one of said $A^1$ or said $A^2$ groups is free of any sulfur atoms and preferably both said $A^1$ and said $A^2$ groups are free of any sulfur atoms. Desirably $A^1$ contains one heterocyclic ring. The hydrocarbyl substituent of the one or more heterocyclic rings can independently be an aromatic, an aliphatic and preferably alkyl, or combinations thereof, e.g., aryl substituted alkyl, alkyl substituted aryl, etc. having from 1 to about 12 carbon atoms. The aromatic substituent can be either attached at one carbon atom, for example phenyl, or an aromatic wherein two of the carbon atoms are actually part of the fused heterocyclic ring system such as in quinoline and lepidine. The aliphatic substituent desirably is an alkyl having from 1 to 6 carbon atoms and preferably is methyl. Examples of electron withdrawing radicals include chloro, fluoro, methoxycarbonyl, and the like. Examples of electron releasing radicals include methoxy, ethoxy, phenoxy, dimethylamino, phenylamino, and the like. Examples of such suitable $A^1$ groups include triazinyl, pyrazyl, pyridazyl, pyrimidyl, methylpyrimidyl, dimethylpyrimidyl, pyridyl, picolyl, quinolyl, lepidyl, dimethylpyridyl, phenylpyridyl, methoxypyridyl, chloropyridyl, and the like. $A^1$ groups include pyridyl, picolyl, and quinolyl. $A^2$ can generally be the same as $A^1$ and hence independently is defined as the same immediately set forth hereinabove.

In lieu of the above definition of $A^1$, alternatively $A^1$ can be thiazyl such as benzothiazyl, or dithiocarbamoyl.

R can be a hydrogen atom, additionally, R can be a hydrocarbyl, for example, an aliphatic, a cycloaliphatic, an aromatic substituted aliphatic, and the like, having from 1 to 16 carbon atoms and preferably from 1 to 6 carbon atoms. An alkyl radical is preferred. When R is an aromatic or an alkyl substituted aromatic, it has from 6 to 16 carbon atoms and preferably from 6 to 10 carbon atoms. One or more of the carbon atoms of the hydrocarbyl radical can be replaced by an oxygen atom, a nitrogen atom, or a substituted nitrogen atom wherein the substituent group is an alkyl and with the nitrogen atom forms a heterocyclic ring having a total of from 1 to 7 carbon atoms. R can also be a hydrocarbyl radical containing from 1 to 16 carbon atoms, as noted above, and containing substituents such as halogen, amino, cyano, alkoxy, hydroxy, or alkoxycarbonyl, and the like. R can also be $A^1$ as defined hereinabove. Of the various R radicals, preferably R is an alkyl having from 1 to 8 carbon atoms such as methyl, ethyl, propyl, isopropyl, butyl, sec-butyl, t-butyl, amyl, hexyl, cyclohexyl, heptyl, octyl, benzyl, phenyl, and the like, including various isomers thereof. In accordance with the above description of $A^1$, $A^2$, and R, examples of heterocyclic thiol-based sulfenimide compounds include N,N-bis(2-pyridyl)-t-butyl sulfenimide, N,N-bis(2-pyridyl)-isopropyl sulfenimide, N,N-bis(2-pyridyl)-cyclohexyl sulfenimide, N,N-bis(2-quinolyl)-t-butyl sulfenimide, and N,N-bis(2-lepidyl)-t-butyl sulfenimide.

A method of making or preparing the heterocyclic thiol-based sulfenimides of the present invention is via a solution reaction in an inert atmosphere. The atmosphere can generally be nitrogen, helium, or argon. The starting compound is a disulfide having a heterocyclic radical substituted on each sulfur atom, that is $A^1$ and $A^2$. The heterocyclic disulfide is reacted with a chlorine source. The chlorine source can be chlorine gas, or chlorine-containing compounds such as sulfuryl chloride. When a chlorine-containing compound is utilized, generally an amide type compound such as urea, dimethylformamide, and the like is utilized as a catalyst. The amount of the chlorine gas or chlorine-containing compound is generally an equivalent amount or a slight excess as from about 0.90 to about 1.1 equivalents for every 1 equivalent of the heterocyclic disulfide. If the amide type catalyst is utilized, only a small amount thereof, such as from about 0.05 to about 1 or 2 percent by weight based upon the total weight of the reactants, is utilized. The reaction is carried out in the presence of an inert solvent, that is, a solvent which is unreactive with respect to chlorine. Suitable solvents are generally non-polar hydrocarbons, desirably aromatic or aliphatic hydrocarbons having a total of from about 5 or 6 to about 25 carbon atoms such as hexane, heptane, octane, nonane, decane, etc., benzene, toluene, cyclohexane, naphtha, the various kerosenes, and the like, as well as chlorinated hydrocarbons having from 1 to 6 carbon atoms and from 1 to 4 halogen atoms such as carbon tetrachloride, methylene chloride, chloroform, chlorobenzene, dichlorobenzene, trichlorobenzene, and the like. The reaction is carried out generally under stirring at normal or slightly elevated pressure under mild temperatures as from about 40° C. to about 90° C., with from 60° C. to about 80° C. being preferred, for a sufficient amount of time to yield a heterocyclic sulfenyl chloride compound. The amount of reaction time is generally from about 10 or 20 minutes to 3 or 4 hours. After formation of the heterocyclic sulfenyl chloride compound, the solution is cooled to room temperature. The reaction time is generally 10, 20 or 30 minutes to about 3 or 4 hours.

The $A^1$ or $A^2$ heterocyclic sulfenyl chloride solution is subsequently reacted with a primary amine wherein the hydrocarbyl group is R, as set forth hereinabove and accordingly fully incorporated by reference, along with a reaction acid acceptor. The amount of the primary amine is generally about one equivalent for every two equivalents of the heterocyclic sulfenyl chloride compound although a slight excess thereof can be utilized to ensure complete reaction of all the primary amine. The reaction acid acceptor is generally an amine compound such as triethylamine, pyridine, dimethylaniline, and the like having from 3 to 15 carbon atoms. The amount of the acid acceptor is generally at least two equivalents as from about 2.0 to about 2.5 equivalents for every one equivalent of the primary amine. Alternatively, the acid acceptor can be a primary amine and thus the equivalent ratio is from about 3.0 to about 3.5 for every two equivalent of the sulfenyl chloride. The reaction with the primary amine is generally carried out in the presence of additional inert solvent which can be either added directly to the reaction vessel, or along with the primary amine, or both. Inasmuch as this reaction is very rapid, low reaction temperatures such as from about minus 40° C. to about plus 15° C. are utilized. The yield generally varies with reaction time which can be anywhere from one to approximately 16 hours. Yields are typically 80 percent or greater. The salt such as triethylamine hydrochloride which is retained after filtering is washed with additional solvent such as carbon tetrachloride. The removed solvent, including the wash solvent, is then generally evaporated off as by the utilization of reduced pressure, heat, or both, thereby leaving the heterocyclic thiol-based sulfenimide compound.

The heterocyclic thiol sulfenimides described in this invention may also be prepared by methods other than that noted above. Other methods include those described in U.S. Pat. No. 2,860,142 and U.S. Pat. No. 3,875,177 which involves the treatment of an N-substituted monosulfenamide with a carboxylic acid anhydride. Another method which can be used to prepare such sulfenimides is described in U.S. Pat. No. 3,151,122 and involves the treatment of N-monosulfenamides with a strong acid.

The heterocyclic thiol-based sulfenimide compounds of the present invention are ideally suited for use as a primary accelerator in the cure or vulcanization of rubber. Generally any type of rubber can be utilized such as natural rubber, synthetic rubber, various blends of synthetic rubber, and combinations thereof. Natural rubber, of course, is obtained from plants, trees, and shrubs generally grown in the tropics or hot portions of the earth. Synthetic rubbers include those made from various dienes such as those having from 4 to 12 carbon atoms and preferably from 4 to 8 carbon atoms including 1,3-butadiene, isoprene, 2,3-dimethyl-1,3-butadiene, 2-methyl-1,3-pentadiene, 3,4-dimethyl-1,3-hexadiene, 4,5-diethyl-1,3-octadiene, phenyl-1,3-butadiene, pentadiene, hexadiene, octadiene, and the like. Synthetic rubbers also include copolymers made from the immediately above-noted dienes having from 4 to 12 carbon atoms with a vinyl substituted aromatic compound having from 8 to 20 carbon atoms such as styrene, alphamethylstyrene, 4-n-propylstyrene, 4-t-butylstyrene, 4-dodecylstyrene, 4-p-tolylstyrene, 4-phenylstyrene, and the like, 1-vinylnaphthalene, 2-vinylnaphthalene, and the alkyl, cycloalkyl, aryl, alkaryl, and the aralkyl derivatives thereof in which the total number of carbon atoms and the combined substituents is generally not greater than 12 carbon atoms.

Another class of synthetic rubbers which can be utilized in the present invention are EPDM rubbers. These are polymers made from ethylene, propylene, and a non-conjugated diene monomer such as norbornene, methylnorbornene, ethylidenenorbornene, dicyclopentadiene, and the like. Other sulfur vulcanizable rubbers known to the art and to the literature can also be utilized.

The rubber polymers made from conjugated dienes or copolymers of a conjugated diene or the vinyl substituted aromatic are preferably "elastomeric" materials, that is they conform, when vulcanized, to the definition of an elastomeric or rubber material found in ASTM D 1566.

As noted above, either natural rubber, one or more synthetic rubbers, that is either a single type of synthetic rubber or blends of two or more synthetic rubbers, as well as a blend of natural rubber and one or more synthetic rubbers can be cured utilizing the heterocyclic thiol-based sulfenimide compounds of the present invention as a primary accelerator. When utilized as an accelerator, the amount thereof is generally from about 0.1 to about 10 and preferably from about 0.2 to about 2.0 parts by weight per 100 parts by weight of the rubber polymer or blend. When the sulfenimides of the invention are utilized as accelerators for curing rubber compounds, the natural or synthetic rubber compositions of the present invention generally contain other conventional compounding ingredients in conventional amounts, both of which are well known to the art and to the literature. For example, various fillers and reinforcing agents, such as clay, silica, and carbon black, can be utilized in amounts up to about 200 phr. Various oils, for example aromatic, naphthenic, or paraffinic, can be utilized to plasticize the rubber in amounts up to about 200 phr. Various activators such as zinc oxide, stearic acid, and the like, can also be used in amounts up to about 15 or more phr. Various antidegradants, and the like, can also be utilized. Such materials are generally mixed into the rubber by utilizing a mill, a Banbury mixer, or the like.

When utilized as a primary accelerator in combination with the one or more types of rubber noted hereinabove, the rubber compositions can be used in a large number of applications, including finished articles such as tires.

The heterocyclic thiol-based sulfenimides of the present invention when utilized as primary accelerators with rubber have been found to yield very much improved cure rates, i.e., lower t25-t2 values and higher Vmax values. The improved cure rate values were generally superior to the values obtained utilizing conventional sulfenamide primary accelerators such as 2-mercaptobenzothiazolyl cyclohexyl sulfenamide, 2-mercaptobenzothiazolyl tertiary-butyl sulfenamide, N,N- bis(2-benzothiazolyl)-t-butyl-sulfenimide, and the like. Another unexpected result was that improved scorch delay was obtained. Yet another unexpected result was reduced reversion values as set forth in the following data.

The invention will be better understood by reference to the following examples in which all parts are by weight and all temperatures are in degrees Celsius, unless otherwise specified.

EXAMPLES

Various heterocyclic sulfenimides of the present invention were tested in accordance with appropriate ASTM procedures for rubber. Parameters which characterize vulcanization were taken from ODR (oscillating disc rheometer) cure curves ("rheographs"), which were obtained for vulcanization at 153° C. and/or 160° C. The parameters Rmin and Rmax are the minimum rheometer torque (before the onset of vulcanization) and the maximum rheometer torque (due to vulcanization), respectively. The parameter t2 is the time required for an increase (over Rmin) in rheometer torque of 2.2 dNm joule (2.0 in-lb); t25 is the time required for the occurrence of 25 percent of the increase in torque due to vulcanization (time at which torque equals (Rmax-Rmin) 0.25+Rmin); t90 is the time required for the occurrence of 90 percent of the increase in torque due to vulcanization (time at which torque equals (Rmax-Rmin) 0.9+Rmin). Vmax is the maximum slope of the vulcanization curve, expressed in terms of a percent of Rmax-Rmin per minute.

The invention will be better understood by reference to the following examples in which all parts are per 100 parts by weight of rubber (phr) and all temperatures are in degrees Celsius, unless otherwise specified.

Preparation of Rubber Masterbatches for Accelerator Evaluation

The various examples of heterocyclic thiol-based sulfenimide accelerators which were prepared were tested in typical NR and SBR carbon-black reinforced compounds.

Masterbatch SBR

An SBR rubber masterbatch was prepared, based on SBR-1500, and the SBR masterbatch contained the following ingredients:

| SBR Masterbatch | Parts |
|---|---|
| SBR-1500 | 100.0 |
| Carbon Black N-330 | 50.0 |
| Circosol 4240, a Naphthenic Oil, ASTM D2226, Type 103 | 10.0 |
| Zinc Oxide | 4.0 |
| Stearic Acid | 2.0 |
| Total | 166.0 |

The SBR masterbatch was prepared by mixing the above-noted components in a Banbury mixer according to standard techniques. Subsequently, various accelerators, sulfur, and an antidegradant were added on a laboratory roll mill in the amounts set forth hereinbelow and blended by using standard laboratory mill mixing techniques.

| | Parts |
|---|---|
| SBR-Masterbatch | 166.0 |
| SANTOFLEX 13 | 2.0 |
| Sulfur | 2.0 |

-continued

| | Parts |
|---|---|
| Accelerators | As indicated |

SBR-1500 is a cold emulsion-polymerized, non-pigmented styrene/butadiene copolymer rubber containing nominally 23.5 percent bound styrene;

SANTOFLEX ® 13 is N-(1,3-dimethylbutyl)-N'-phenyl-para-phenylenediamine, an antidegradant.

In a similar manner, a natural rubber masterbatch was made:

| Natural Rubber Masterbatch | Parts |
|---|---|
| Natural Rubber (SMR-CV) | 100.0 |
| Carbon Black N-330 | 50.0 |
| Naphthenic Oil; Circosol 4240 | 5.0 |
| Zinc Oxide | 5.0 |
| Stearic Acid | 2.0 |
| Total | 162.0 |

The natural rubber masterbatch was blended with the following compounds according to standard laboratory mill-mixing techniques.

| | Parts |
|---|---|
| Natural Rubber Masterbatch | 162.0 |
| SANTOFLEX 13 | 2.0 |
| Sulfur | 2.5 |
| Accelerators | As indicated |

An SBR/BR masterbatch was prepared, based on SBR-1712 containing the following ingredients:

| Masterbatch SBR/BR | |
|---|---|
| SBR 1712 | 89.0 |
| BR 1203 | 35.0 |
| N-330 Black | 65.0 |
| Sundex 790 | 10.0 |
| Zinc Oxide | 3.0 |
| Stearic Acid | 1.0 |
| Sunlite 240 | 2.0 |
| Santoflex 13 | 2.0 |
| Total | 207.0 |

The SBR/BR masterbatch was prepared by mixing the above-noted components in a Banbury mixer according to standard techniques. Subsequently, various accelerators, sulfur, and an antidegradant were added on a laboratory roll mill in the amounts set forth hereinbelow and blended by using standard laboratory mill mixing techniques.

| | Parts |
|---|---|
| SBR/BR Masterbatch | 207.0 |
| Sulfur | 2.0 |
| Accelerators | as indicated |

SBR-1712 is a cold emulsion-polymerized, non-pigmented styrene/butadiene copolymer rubber containing nominally 23.5 percent bound styrene;

BR 1203 is a solution polybutadiene of high cis content.

Sundex 790 is an aromatic oil, ASTM D2226, type 101.

Sunlite 240 is a blend of petroleum waxes produced by WITCO.

Test data for various heterocyclic thiol-based sulfenimides as SBR and NR accelerators are summarized in Tables I through IX. The control stock contained a conventional sulfenamide accelerator or N,N-bis(2-benzothiazolyl)-t-butyl-sulfenimide. The control stock was prepared from the same masterbatch as was the experimental stock and measured in the same set on the same day as was the experimental stock.

EXAMPLE 1

N,N-Bis(2-Pyridylthiyl)-t-Butyl Sulfenimide

Sulfuryl chloride (30.65 g., 0.22 moles) and urea catalyst (300 mg.) were added to reagent grade carbon tetrachloride (700 ml) in a 2 liter, three-necked flask equipped with mechanical stirrer, condenser, and heating mantle controlled by a Thermowatch ® device. Then charged to the flask was 2,2'-pyridyl disulfide (50 g., 0.22 moles). The mixture was gradually heated to 70° C. and maintained at this temperature for three hours, while off-gases were vented. At the end of this time, the orange slurry/solution was transferred to a dropping funnel and added to a three-necked flask containing a mixture of t-butylamine (16.6 g, 0.22 moles) and triethylamine (50.4 g) as an acid acceptor in 150 ml carbon tetrachloride. The temperature was maintained at minus 5° C. to about 5° C. over the course of 2.25 hours by the use of an ice/reethanol cooling bath and by adjusting the rate of addition. After the addition of the 2-pyridyl sulfenyl chloride was completed, the slurry was stirred overnight.

The next day the slurry was filtered from precipitated triethylamine hydrochloride and evaporated under reduced pressure to give 54.2 g of light brown solid, m.p. 85°–110° C., over 90 percent pure by liquid chromatographic analysis. The compound gave a characteristic nuclear magnetic resonance spectrum (chemical shift δ, multiplicity, assignment, integration) 6.8–8.6, m, aromatic, 8 H; 1.4, s, t-butyl, 9 H.

EXAMPLE 2

N,N-Bis(2-Pyridyl)-Cyclohexyl Sulfenimide

A solution containing pyridyl sulfenyl chloride (32.9 g, 0.226 moles) was prepared as in Example 1 in carbon tetrachloride solution and transferred to a dropping funnel. The solution was added to a mixture of cyclohexylamine (11.2 g, 0.113 moles), triethylamine (25.2 g) and carbon tetrachloride (75 ml). The temperature was maintained at minus 10° C. to minus 5° C. using an isopropanol/dry ice bath. After overnight stirring at room temperature, the triethylammonium chloride was removed by filtration, and the solvent evaporated under reduced pressure to give a nearly quantitative yield of the crude sulfenimide. Recrystallization from acetonitrile gave material m.p. 72°–74° C. NMR:(chemical shift δ, multiplicity, assignment, integration) 6.8–8.6, m, aromatic, 8H; 3.3, m, methine, 1 H, 1.0–2.2, m, methylene, 10 H.

EXAMPLE 3

N,N-Bis(2-Pyridyl)-Isopropyl Sulfenimide

A solution of 2-pyridyl sulfenyl chloride in carbon tetrachloride was made up as in Example 1, starting from 50 g. of 2-pyridyl disulfide, and the solution was stored for two days in the refrigerator before use. The solution was then brought to room temperature, placed in a dropping funnel, and added to a mixture of isopropylamine (13.4 g., 0.22 moles), triethylamine (50.4 g) and carbon tetrachloride (150 ml) at minus 5° C. to plus 10° C. After stirring overnight at room temperature, the solids were removed from the reaction medium by filtration. The solution was then evaporated under reduced pressure (using a rotary evaporator) and decanted away from a small amount of dark oil which separated. The product was obtained as a thick oil which partially solidified upon cooling in the refrigerator. A crystalline product was obtained by dissolving the thick oil in hexane at room temperature and allowing the solution to cool while evaporating on the rotary evaporator under aspirator pressure. The solution was decanted from any oil which separated, and the recrystallized product collected by filtration. It had nearly the same melting point as 2,2'-pyridyl disulfide, 56°–58° C. NMR: (Chemical shift δ multiplicity, assignment, integration) 6.8–8.6, m, aromatic, 8H; 3.8, m, methine, 1H; 1.3, d, methyl, 6H.

EXAMPLE 4

N,N-Bis(2-Quinolyl)-t-butyl Sulfenimide

2-Quinolyl disulfide (17.1 g., 0.053 moles) was converted to the sulfenyl chloride by refluxing with sulfuryl chloride (7.2 g., 0.053 moles) in carbon tetrachloride (170 ml) containing dimethylformamide (0.07 g) for three hours with provision for gas evolution. The solvent was stripped off under vacuum to give an orange oil which was redissolved in carbon tetrachloride (42 ml).

This solution was placed in a dropping funnel and added over thirty minutes to a three-necked flask equipped with stirrer and thermometer and containing t-butylamine (3.9 g, 0.053 moles), triethylamine (14.2 g), and dimethylformamide (106 ml). The contents of the flask were protected from moisture and cooled to 0° C. in an ice/reethanol bath. The mixture was stirred for 30 minutes at room temperature and transferred to a beaker fitted with a mechanical stirrer. Ice water (850 ml) was added and the cold mixture extracted twice with 200 ml portions of chloroform. The chloroform solution was washed with water (3 portions totaling 1 liter), and dried over anhydrous sodium sulfate. Evaporation of the solvent gave crude product (25.5 g) which was washed with acetonitrile (100 ml) and treated with anhydrous diethyl ether (300 ml). After filtering off the white solid impurity from the solution, and further washings and extractions with ether, 8.1 g of product, m.p. 105°–115° C. was obtained. This was analyzed by liquid chromatography and NMR spectroscopy: (chemical shift δ, multiplicity, assignment, integration) 7.2–8.1, m, aromatic, 12H; 1.5, s, t-butyl, 9H.

EXAMPLE 5

N,N-Bis(4-Methyl-2-Quinolyl)-t-Butyl Sulfenimide

In this Example, the common name "lepidine" is used to refer to the structure 4-methylquinoline. 4-methyl-2-quinolinethiyl-t-butyl sulfenamide was prepared using conventional technology to effect the oxidative coupling of 2-mercaptolepidine and t-butylamine. It was routinely isolated in approximately 85 percent purity, as measured by NMR and LC, m.p. 111°–115° C.

About 25 grams of the crude lepidine-t-butyl sulfenamide (containing about 20 g of the pure compound by NMR) was dissolved in chloroform (75 ml) and acetic anhydride (10.3 g) was added to the solution. The solution was allowed to stand at room temperature for 20.5 hours, when it was diluted to 100 ml volume with additional chloroform, washed with two equal volumes of 5 percent sodium bicarbonate solution, and dried over anhydrous sodium sulfate. The chloroform solution was mixed with hexane (200 ml) and a small first crop of solid filtered off. The reaction mixture was then fractionally crystallized by concentration under reduced pressure. A main fraction (11.9 g) was isolated of 95 area percent purity by liquid chromatography, m.p. 136°–142° C., NMR: (chemical shift δ, multiplicity, assignment, integration) 7.3–8, m, aromatic, 10H; 2.5, s, methyl, 6H; 1.5, S, t-butyl, 9H.

EXAMPLE 6

N-(2-Pyridyl)-N-(2-Benzothiazolyl)-t-Butyl-Sulfenimide

A 500-ml, three-necked flask was fitted with a condenser, thermometer and gas inlet valves. After the vessel had been evacuated and flushed with nitrogen, 250 ml of nitrogen-purged $CCl_4$ was added along with 12.5 g of 2,2'-dipyridyl disulfide, 0.10 g of urea, and 7.7 g of $SO_2Cl_2$. The solution was heated to 70° C. with stirring for three hours. The resulting homogeneous orange solution was then cooled in an ice bath to about 10° C. The condenser was removed and replaced with an addition funnel containing 27.2 g of 2-mercaptobenzothiazolyl-t-butyl sulfenamide slurried in a 100-ml solution of $CCl_4$ containing 11.5 g of triethylamine. The slurry was added to the solution of 2-pyridyl sulfenyl chloride over a half hour such that the temperature of the reaction mixture did not exceed 10° C. The mixture was allowed to warm to room temperature and stirred for 16 hours. At this time, it was filtered and the filter cake was washed with fresh $CCl_4$ until the liquid emerging from the filter was colorless. The $CCl_4$ filtrate was stripped under reduced pressure leaving a golden-brown viscous oil which solidified upon trituration with pentane. The resulting yellow solid was filtered and dried. The weight of N-(2-pyridyl)-N-(2-benzothiazolyl)-t-butylsulfenimide was 29.5 g, 75 percent yield. NMR: (chemical shift δ, multiplicity, assignment, integration) 8.47, d, aromatic, 1H; 6.9–7.9, m, aromatic, 7H; 1.45, s, t-butyl, 9H. Mass Spect: $M^+ = 348$. The compound showed a single unique and discrete peak when analyzed by liquid chromatography.

EXAMPLE 7

N,N-Bis(4,6-Dimethyl-2-Pyrimidyl)-t-Butyl Sulfenimide 4,6-dimethyl-2,2'-pyrimidine disulfide (27.8 g. 0.1 mole) was charged into a mixture of sulfuryl chloride (13.5 g, 0.1 mole), urea (120 mg) and carbon tetrachloride (300 ml), was heated for two hours at 70° C. in a reaction flask equipped with mechanical stirrer and protected from atmospheric moisture by a Drierite ® tube. The reaction solution was filtered from green insoluble solid (8.0 g) and placed in a three-necked reaction flask equipped with magnetic stirrer and protected from atmospheric moisture. At a temperature of 5°–10° C., a solution of t-butylamine (7.3 g, 0.1 moles) and triethylamine (25 g) dissolved in carbon tetrachloride (50 ml) was added dropwise. After stirring overnight, the solution was filtered from solids and evaporated under reduced pressure. Solid impurities were removed by filtration of an ether solution of the crude product to give a clear oil product (10.4 g), estimated by NMR to be approximately 25 percent of the sulfenimide and 75 percent of the sulfenamide. A portion of this product (6.3 g) was combined with triethylamine (4.0 g) in carbon tetrachloride (15 ml) and added to a filtered preparation of crude 4,6-dimethyl-2-sulfenyl chloride prepared from the corresponding disulfide (6.35 g, 0.023 moles) in carbon tetrachloride solution as described above. A water bath was used to control the temperature of this second addition at 25°–30° C. After stirring overnight and filtering the reaction solution, the crude product (9 g) was obtained upon evaporation of the solvent as a thick oil which crystallized on standing. Treatment of the crude product with acetonitrile (25 ml) and collection of the undissolved solid yielded the pure sulfenimide (2.8 g), m.p. 166°–176° C., a single component by LC analysis. NMR: (chemical shift δ, multiplicity, assignment, integration) 6.65, s, aromatic, 2H; 2.4, s, methyl, 12H; 1.4, s, t-butyl, 9H.

EXAMPLE 8

N,N-Bis(2-Pyrimidyl)-t-Butyl Sulfenimide

A solution of sulfuryl chloride (10.2 g, 0.075 moles) in carbon tetrachloride (100 ml) was made up in a round bottom reaction flask, then urea (100 mg) and 2-pyrimidyl disulfide (16.7 g 0.075 moles) was added. The mixture was heated to 70° C. for one hour with provision made for venting the off-gases. The thus formed sulfenyl chloride solution was then placed in a dropping funnel and added to a mixture of t-butylamine (5.0 g, 0.068 moles) and triethylamine (16.7 g) in carbon tetrachloride (50 ml). The reaction was carried out in a three-necked reaction flask, equipped with mechanical stirring and protected from atmospheric moisture. An ice/reethanol cooling bath was used to control the temperature of the reaction at minus 5° C. to plus 5° C. After stirring the reaction mixture overnight at room temperature, the crude product was recovered by evaporation of the solvent after the precipitated salts had been removed by filtration. The salt filter cake was washed with additional solvent (CCl₄, 80 ml).

Analysis of the crude reaction product by NMR and liquid chromatography indicated the presence of considerable sulfenamide. The yield of crude product was 7.9 g. It was combined with equivalent material from a previous reaction to make 10.8 g of mixed sulfenamide/sulfenimide product and dissolved in CCl₄ (120 ml) and triethylamine (1.2 g). A small amount of additional sulfenyl chloride was made in the above manner in CCl₄ solution from 2-pyrimidyl disulfide (1.3 g) and sulfuryl chloride (0.6 ml). The sulfenyl chloride solution was added dropwise to the mixed sulfenamide/sulfenimide/triethylamine solution at minus 5° to plus 5° C. and the reaction stirred overnight. The precipitated salts were removed by filtration and the solvent evaporated under reduced pressure to give 7.5 g crude product. This was stirred with acetonitrile (31.5 ml) at room temperature to give 3.2 g of purified product which was collected by filtration. The sulfenimide, mp 140°–143° C. was shown to be pure by LC and characterized by NMR: (chemical shift δ, multiplicity, assignment, integration) 7.0 and 8.6, m, aromatic, 6H; 1.4, s, t-butyl, 9H.

Curing data utilizing the sulfenimide accelerators of Examples 1-8 are set forth in Tables I-IX.

TABLE I

Compounds of Examples 1, 2 and 3 in Natural Rubber and SBR

| | | | | | | | | |
|---|---|---|---|---|---|---|---|---|
| SBR Masterbatch | 166 | 166 | 166 | 166 | — | — | — | — |
| NR Masterbatch | — | — | — | — | 162 | 162 | 162 | 162 |
| Santocure NS (control) | 1.2 | — | — | — | 0.6 | — | — | — |
| Compound Example 1 | — | 1.2 | — | — | — | 0.6 | — | — |
| Compound Example 2 | — | — | 1.2 | — | — | — | 0.6 | — |
| Compound Example 3 | — | — | — | 1.2 | — | — | — | 0.6 |
| Mooney Scorch, 121° C., t5, min | 70.0 | 85.5 | 88.6 | 90.4 | 35.6 | 40.0 | 41.4 | 43.5 |
| ODR Data at 153° C. | | | | | | | | |
| Rmax, Nm | 4.11 | 4.65 | 4.61 | 4.70 | 3.73 | 4.31 | 4.30 | 4.41 |
| Rmin, Nm | 0.67 | 0.65 | 0.67 | 0.66 | 0.67 | 0.62 | 0.66 | 0.64 |
| t90, min | 24.7 | 30.3 | 28.5 | 27.8 | 13.5 | 11.8 | 11.8 | 11.7 |
| t2, min | 11.5 | 13.8 | 13.2 | 13.5 | 6.2 | 6.3 | 6.3 | 6.5 |
| t90-t2 min | 13.2 | 16.5 | 15.3 | 14.3 | 7.3 | 5.5 | 5.5 | 5.2 |
| t25 min | 14.7 | 16.7 | 15.5 | 16.0 | 7.7 | 7.5 | 7.3 | 7.7 |
| t25-t2 min | 3.2 | 2.9 | 2.3 | 2.5 | 1.5 | 1.2 | 1.0 | 1.2 |
| Max. veloc. of vulc., %/min | 12.4 | 16.6 | 18.4 | 20.0 | 21.4 | 37.5 | 37.5 | 39.8 |
| ODR Data at 160° C. | | | | | | | | |
| Reversion, %/30 min. | — | — | — | — | 24.2 | 20.3 | 18.6 | 18.2 |

TABLE II

Compound of Example 4 in NR and SBR

| | | | | |
|---|---|---|---|---|
| SBR Masterbatch | 166 | 166 | — | — |
| NR Masterbatch | — | — | 162 | 162 |
| Santocure NS | 1.2 | — | 0.6 | — |
| Compound Example 4 | — | 1.2 | — | 0.6 |
| Mooney Scorch, 135° C., t5, min. | 25.1 | 33.0 | 12.5 | 10.5 |
| ODR Data at 153° C. | | | | |
| Rmax, Nm | 4.04 | 4.11 | 3.68 | 3.92 |
| Rmin, Nm | 0.61 | 0.63 | 0.67 | 0.69 |
| t90, min | 22.8 | 28.5 | 12.5 | 10.7 |
| t2, min | 10.3 | 11.8 | 5.3 | 4.8 |
| t90-t2 min | 12.5 | 16.7 | 7.2 | 5.9 |
| t25 min | 13.5 | 14.8 | 6.7 | 6.0 |
| t25-t2 min | 3.2 | 3.0 | 1.4 | 1.2 |
| Max. veloc. of vulc., %/min | 13.2 | 14.8 | 22.8 | 27.7 |
| ODR Data at 160° C. | | | | |
| Reversion, %/30 min. | — | — | 25.6 | 21.2 |

TABLE III

Compound of Example 5 in NR and SBR

| | | | | |
|---|---|---|---|---|
| SBR Masterbatch | 166 | 166 | — | — |
| NR Masterbatch | — | — | 162 | 162 |
| Santocure NS | 1.2 | — | 0.6 | — |
| Compound Example 5 | — | 1.2 | — | 0.6 |
| Mooney Scorch, 121° C., t5, min. | 77.0 | 104.9 | 40.5 | 42.5 |
| ODR Data at 153° C. | | | | |
| Rmax, Nm | 4.05 | 4.16 | 3.57 | 3.84 |
| Rmin, Nm | 0.66 | 0.67 | 0.55 | 0.59 |
| t90, min | 25.5 | 31.8 | 13.5 | 12.5 |
| t2, min | 12.2 | 13.2 | 6.3 | 6.0 |
| t90-t2 min | 13.3 | 18.6 | 7.2 | 6.5 |
| t25 min | 15.7 | 16.7 | 7.7 | 7.2 |
| t25-t2 min | 3.5 | 3.5 | 1.4 | 1.2 |

TABLE III-continued

Compound of Example 5 in NR and SBR

| | | | | |
|---|---|---|---|---|
| Max. veloc. of vulc., %/min | 12.5 | 12.9 | 21.4 | 25.9 |
| ODR Data at 160° C. | | | | |
| Reversion, %/30 min. | — | — | 26.9 | 23.4 |

TABLE IV

Compound of Example 6 in NR and SBR

| | | | | |
|---|---|---|---|---|
| SBR Masterbatch | 166 | 166 | — | — |
| NR Masterbatch | — | — | 162 | 162 |
| Santocure NS | 1.2 | — | 0.6 | — |
| Compound Example 6 | — | 1.2 | — | 0.6 |
| Mooney Scorch, 121° C., t5, min. | 69.6 | 71.5 | 36.5 | 36.6 |
| ODR Data at 153° C. | | | | |
| Rmax, Nm | 4.00 | 4.39 | 3.48 | 3.75 |
| Rmin, Nm | 0.60 | 0.59 | 0.49 | 0.46 |
| t90, min | 25.7 | 26.3 | 12.8 | 12.2 |
| t2, min | 12.0 | 11.3 | 6.0 | 6.0 |
| t90-t2 min | 13.7 | 15.0 | 6.8 | 6.2 |
| t25 min | 15.3 | 14.7 | 7.2 | 7.2 |
| t25-t2 min | 3.3 | 3.4 | 1.2 | 1.2 |
| Max. veloc. of vulc., %/min | 12.0 | 13.0 | 22.8 | 27.3 |
| ODR Data at 153° C. | | | | |
| Reversion, %/30 min. | — | — | 16.6 | 14.2 |

TABLE V

Compound of Example 7 in NR and SBR

| | | | | |
|---|---|---|---|---|
| SBR Masterbatch | 166 | 166 | — | — |
| NR Masterbatch | — | — | 162 | 162 |
| Santocure NS | 1.2 | — | 0.6 | — |
| Compound Example 7 | — | 1.2 | — | 0.6 |
| Mooney Scorch, 135° C., t5, min. | 65.0 | 197.9 | 31.0 | 40.4 |
| ODR Data at 153° C. | | | | |
| Rmax, Nm | 4.62 | 4.42 | 4.16 | 3.92 |
| Rmin, Nm | 0.94 | 1.00 | 0.85 | 0.85 |
| t90, min | 23.9 | 64.0 | 11.7 | 16.4 |
| t2, min | 11.1 | 22.1 | 5.0 | 4.9 |
| t90-t2 min | 12.8 | 41.9 | 6.7 | 11.5 |
| t25 min | 13.7 | 30.5 | 6.3 | 7.5 |
| t25-t2 min | 2.6 | 8.4 | 1.3 | 2.6 |
| Max. veloc. of vulc., %/min | 12.1 | 5.0 | 23.5 | 10.9 |
| ODR Data at 160° C. | | | | |
| Reversion, %/30 min. | — | — | 26.8 | 11.6 |

TABLE VI

Compound of Example 8 in SBR and NR

| | | | | |
|---|---|---|---|---|
| SBR Masterbatch | 166 | 166 | — | — |
| NR Masterbatch | — | — | 162 | 162 |
| Santocure NS | 1.2 | — | 0.6 | — |
| Compound Example 8 | — | 1.2 | — | 0.6 |
| Mooney Scorch, 121° C., t5, min. | 72.6 | 88.6 | 33.6 | 46.4 |
| ODR Data at 153° C. | | | | |
| Rmax, Nm | 4.76 | 5.08 | 4.11 | 4.12 |
| Rmin, Nm | 0.93 | 0.94 | 0.84 | 0.78 |
| t90, min | 25.7 | 47.0 | 12.4 | 15.8 |
| t2, min | 11.6 | 20.7 | 5.4 | 6.3 |
| t90-t2 min | 14.1 | 26.3 | 7.0 | 9.5 |
| t25 min | 15.3 | 28.3 | 6.7 | 8.4 |
| t25-t2 min | 3.7 | 7.6 | 1.3 | 2.1 |
| Max. veloc. of vulc., %/min | 12.0 | 9.8 | 22.7 | 17.5 |
| ODR Data at 160° C. | | | | |
| Reversion, %/30 min. | — | — | 22.7 | 21.3 |

TABLE VII

Compound of Example 1 at Matched Modulus in NR and SBR

| | | | | |
|---|---|---|---|---|
| SBR Masterbatch | 166 | 166 | — | — |
| NR Masterbatch | — | — | 162 | — |
| Santocure NS | 1.2 | — | 0.6 | — |
| Compound Example 1 | — | 0.6 | — | 0.3 |
| Mooney Scorch, 135° C., t5, min. | 27.0 | 32.0 | 11.5 | 11.5 |
| ODR Data at 153° C. | | | | |
| Rmax, Nm | 4.41 | 4.52 | 4.06 | 4.03 |
| Rmin, Nm | 0.72 | 0.74 | 0.69 | 0.72 |
| t90, min | 24.8 | 33.5 | 11.8 | 13.2 |
| t2, min | 10.7 | 11.8 | 4.6 | 4.6 |
| t90-t2 min | 14.1 | 21.7 | 7.2 | 8.6 |
| t25 min | 13.9 | 14.2 | 5.9 | 5.4 |
| t25-t2 min | 3.2 | 2.4 | 1.3 | 0.8 |
| Max. veloc. of vulc., %/min | 11.4 | 10.0 | 22.2 | 24.0 |
| ODR Data at 160° C. | | | | |
| Reversion, %/30 min. | — | — | 16.4 | 12.8 |

TABLE VIII

Compound of Example 1 in SBR/BR Rubber Blend At Matched Modulus

| | | |
|---|---|---|
| Masterbatch NR/BR | 207.0 | 207.0 |
| Insoluble Sulfur 60 | 2.0 | 2.0 |
| Santocure NS | 1.0 | — |
| Compound Example 1 | — | 0.6 |
| Mooney Scorch, 121° C., t5, min. | 48.0 | 55.0 |
| ODR Data at 153° C. | | |
| Rmax, Nm | 3.51 | 3.60 |
| Rmin, Nm | 0.69 | 0.69 |
| t90, min | 21.0 | 28.3 |
| t2, min | 10.0 | 10.5 |
| t90-t2 min | 11.0 | 17.8 |
| t25 min | 12.2 | 12.2 |
| t25-t2 min | 2.2 | 1.7 |
| Max. veloc. of vulc., %/min | 14.5 | 13.4 |
| ODR Data at 180° C. | | |
| Reversion, %/30 min. | 10.4 | 3.1 |

TABLE IX

Compound of Example 1 Compared to Santocure NS and N,N-bis(2-benzothiozolylthiyl)t-butyl-sulfenimide in SBR

| | | | |
|---|---|---|---|
| SBR Masterbatch | 166.0 | 166.0 | 166.0 |
| Santocure NS | 1.2 | — | — |
| Bis(sulfenamide) | — | 1.2 | — |
| Compound of Example 1 | — | — | 1.2 |
| Mooney Scorch, 121° C., t5, min. | 69.6 | 113.1 | 82.1 |
| ODR Data at 153° C. | | | |
| Rmax, Nm | 4.0 | 4.03 | 4.60 |
| Rmin, Nm | 0.60 | 0.62 | 0.60 |
| t90, min | 25.7 | 35.2 | 30.3 |
| t2, min | 12.0 | 14.5 | 13.0 |
| t90-t2 min | 13.7 | 20.7 | 17.3 |
| t25 min | 15.3 | 21.3 | 15.7 |
| t25-t2 min | 3.3 | 6.8 | 2.7 |
| Max. veloc. of vulc., %/min | 12.0 | 7.3 | 17.1 |

As apparent from the above Tables, the sulfenimide accelerators of the present invention gave excellent cure rates (especially in natural rubber), excellent scorch delay, and reduced reversion.

Similar excellent results were obtained when the heterocyclic thiol sulfenimide accelerators were used to cure blends of natural rubber and butadiene rubber.

While in accordance with the Patent Statutes, the best mode and preferred embodiment has been set forth, the scope of the invention is not limited thereto, but rather by the scope of the attached claims.

What is claimed is:

1. A compound having the formula wherein each of $A_1$ and $A_2$, is pyrimidyl, or said pyrimidyl ring containing (1) one or more hydrocarbyl substituents of from 1 to 12 carbon atoms, or (2) one or more electron withdrawing radicals selected from chloro, fluoro, and methoxycarbonyl, or (3) one or more electron releasing radicals selected from methoxy, ethoxy, phenoxy, dimethylamino and phenylamino, and wherein R is a (a) hydrogen atom, or (b) a hydrocarbyl radical having from 1 to 16 carbon atoms, or (c) the hydrocarbyl radical of (b) containing a halogen, an amino, a cyano, an alkoxy, a hydroxy or an alkoxycarbonyl substituent.

2. The compound of claim 1 in which R is hydrocarbyl radical of 1 to 8 carbon atoms.

* * * * *